United States Patent [19]

Vernamonti

[11] Patent Number: 5,135,508
[45] Date of Patent: Aug. 4, 1992

[54] SYRINGE SAFETY SHEATH

[76] Inventor: F. Lawrence Vernamonti, 520 Stokes Rd., Medford, N.J. 08055

[21] Appl. No.: 692,303

[22] Filed: Apr. 26, 1991

Related U.S. Application Data

[63] Continuation of Ser. No. 569,208, Aug. 20, 1990, abandoned.

[51] Int. Cl.$^5$ ............................................. A61M 5/32
[52] U.S. Cl. ...................................... 604/192; 604/263
[58] Field of Search ...................... 604/192, 187, 263

[56] References Cited

U.S. PATENT DOCUMENTS

| | | | |
|---|---|---|---|
| 4,643,722 | 2/1987 | Smith, Jr. | 604/192 |
| 4,659,330 | 4/1987 | Nelson et al. | 604/192 |
| 4,664,259 | 5/1987 | Landis | 206/365 |
| 4,846,803 | 7/1989 | Emerson | 604/263 |
| 4,875,896 | 10/1989 | Kurtz | 604/187 |

FOREIGN PATENT DOCUMENTS

| | | | |
|---|---|---|---|
| 8800477 | 1/1988 | PCT Int'l Appl. | 604/192 |
| 715350 | 9/1954 | United Kingdom . | |

*Primary Examiner*—John D. Yasko
*Attorney, Agent, or Firm*—Thomas A. Lennox

[57] ABSTRACT

An improved safety sheath to cover syringe needles after use is provided including a body with an opening to receive the used needle with a side handle extending normally from the central lengthwise axis of the body a sufficient distance to allow the health workers' fingers to hold the handle and keep them away from the pointed needle when re-sheathing the syringe. The handle may be hinged as an integral molding to snap into permanent position when used or may wrap around the body when packaged.

12 Claims, 2 Drawing Sheets

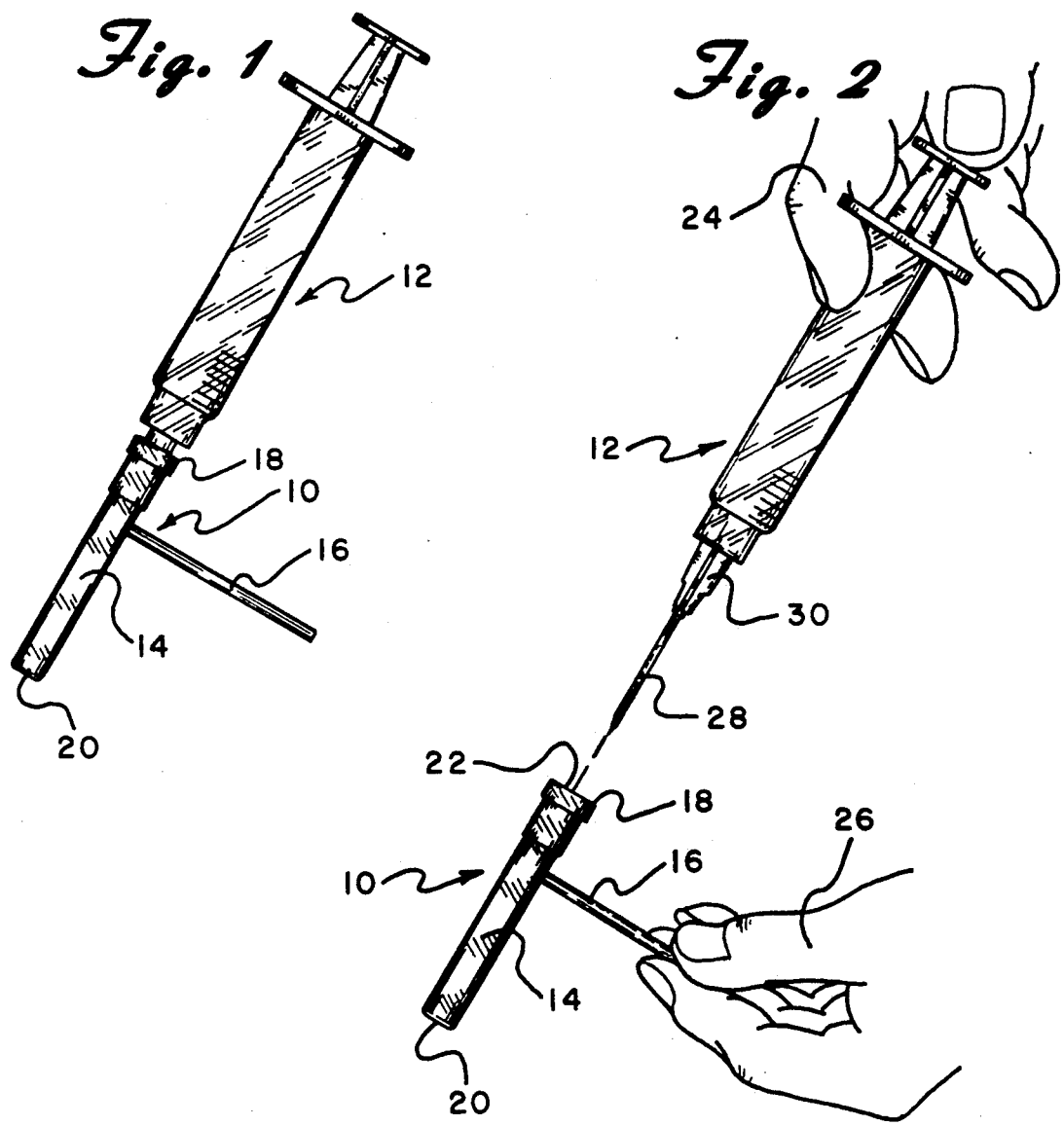
Fig. 1
Fig. 2
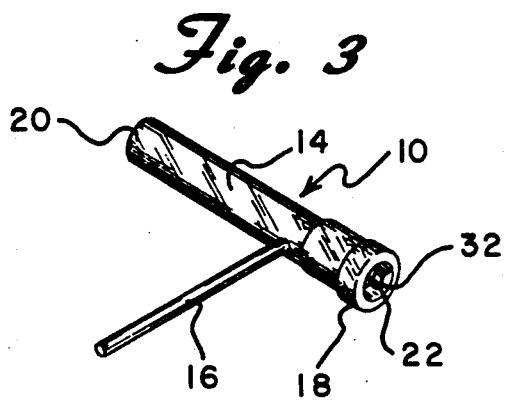
Fig. 3
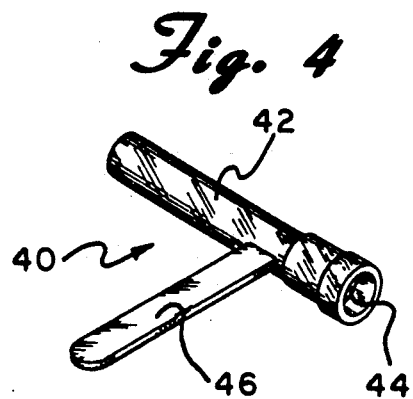
Fig. 4

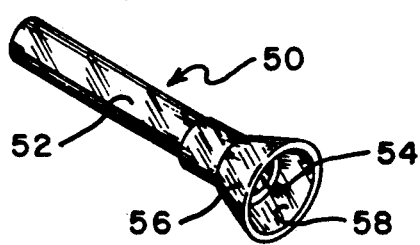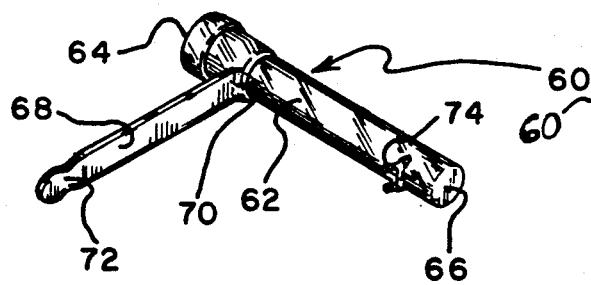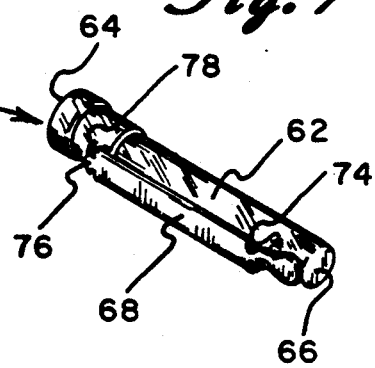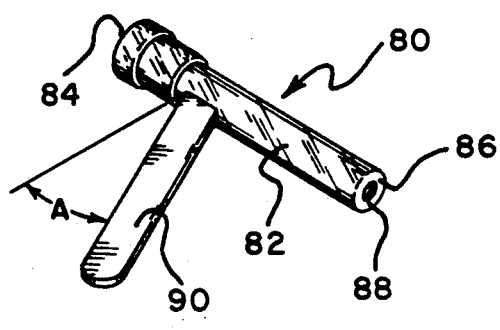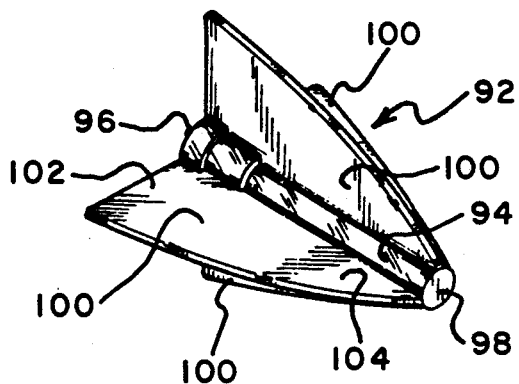

SYRINGE SAFETY SHEATH

BACKGROUND OF THE INVENTION

This invention involves an improved safety sheath for syringes.

The safety hazard to health care workers of accidentally wounding and inoculating themselves with a syringe needle has been recognized for some time. The danger has been well documented and was present when the needles were reusable devices that required sterilization. Mechanical devices and structures were provided to minimize the risk even with those now outmoded devices. Syringes are now disposable devices and are used only on a single patient. It is common to use the same disposable syringe for multiple injections within a short time. Recapping the syringe to protect it from contamination before this reuse poses a risk to the health care worker. Further, the risk to the health care worker also exists during disposal procedures. It is the generally accepted practice and it is required by hospital dictated regulations that the sheath be reapplied over the needle after use. This re-sheathing of the needle is intended to protect trash disposal persons during the handling of the discarded used syringes. A major risk to the health care worker is the process of re-applying the sheath to the used syringe. Since this syringe has been used, in most cases, to pierce a patient's skin it can be contaminated with various types of microbes present in the patient's body that can be a substantial hazard to the health care worker. Although concern for transmission of the Acquired Immune Deficiency Syndrome virus has recently gained substantial publicity, the risk of the health care worker being infected with the hepatitis virus and other microbes have posed a substantial risk for many years.

Various devices have been offered to reduce or possibly eliminate the risk, including devices that break off the needle, that allow the needle to be slid through a slot into the sheath, and more complicated mechanical devices which retract the needle or in other ways reduce the risk.

None of these devices have successfully eliminated the risk and in several cases have substantially increased the cost of the syringe and thus the health care services, many times requiring a more complicated procedure and more time by the health care worker. None of these devices have satisfied the needs described above nor attained the objects described hereinbelow.

SUMMARY OF THE INVENTION

It is an object of the present invention to provide an improved safety sheath for syringes that substantially reduces the risk of the health care worker wounding and inoculating his or her hand during the process of re-applying the sheath to a used syringe needle.

It is a particular object of the present invention to provide a sheath which by a relatively inexpensive and simple modification that will substantially reduce the risk of being punctured by a used hypodermic needle when re-sheathing the syringe.

It is a specific object of the present invention to provide an improved syringe safety sheath which can be molded as an integral part and used on presently available unmodified disposable syringes.

It is a particular object of the present invention to provide a handle that extends transversely from the side of the syringe sheath that may be folded or rolled up when packaged and before use.

A specific object of the present invention is to provide a handle that is hingeably integrally molded with the sheath allowing the handle to swing outwardly normal to the lengthwise central axis of the sheath with a snap detent holding the handle permanently in that position once having been engaged.

An aspect of the invention is a syringe sheath device to cover and protect the needle of a disposable syringe apparatus having a needle holding housing. The device includes a hollow body that includes a length, and a first end with an opening to an interior cavity of the body. The opening and the interior cavity of the body are of sufficient size and shape to receive insertion of the needle and a portion of the needle holding housing. The device further includes gripping means to grip the needle holding housing and hold the hollow body to the syringe apparatus enclosing the needle. The device also includes a handle member attached to the body extending a direction generally radially to a lengthwise central axis of the body, having sufficient strength and rigidity to allow a person to hold the handle member, to insert the needle into the open end of the body, and to engage the gripping means to hold the hollow body to the syringe apparatus. The handle also has a sufficient length to allow the person to hold the handle member with fingers a sufficient distance from the opening to provide a materially decreased risk of accidentally wounding the fingers with the needle as it is inserted into the body.

It is preferred that the device be a single integral molding of a polymeric plastic. It is preferred that the length of the handle member be at least one inch and more preferably about one to about three inches. It is further preferred that the device further include hinge means to hingeably attach a first end of the handle member to the body and locking means to lock the handle member into a position radial to the lengthwise central axis of the body. It is also preferred that the hinge means provide for movement of the handle member to a position proximately parallel to the lengthwise central axis of the body. It is further preferred that the device further including holding means to releasably hold the handle member in a position that the length of the handle is proximately parallel to the lengthwise central axis of the body. It is also preferred that the second end be closed to protect the needle of the syringe inserted therein. It is further preferred that rigidity of handle member be sufficient to allow a person gripping the handle to engage the gripping means of the hollow body to hold the needle holding housing of the syringe. It is also preferred that the handle member be a panel with a width proximate the length of the hollow body. It is further preferred that there be a plurality of handle members all extending symmetrically from the hollow body in directions radially from the center axis of the hollow body. It is also preferred that the handle member be of a thickness and a composition allowing the handle member to wrap around the hollow body when not in use.

Another aspect of the invention is a syringe sheath device including a hollow body that includes a length, a first end with an opening to an interior cavity of the body, and a second closed end. The opening and the interior cavity of the body are of sufficient size and shape to receive insertion of the needle and a portion of the needle holding housing. The device further includes gripping means to grip the needle holding housing and hold the hollow body to the syringe apparatus enclosing the needle, and a handle member attached to the body. The handle member extends a direction generally radially to a lengthwise central axis of the body and has sufficient strength and rigidity to allow a person to hold the handle member, and insert the needle into the open end of the body. The handle member has sufficient length to allow the person to hold the handle member with fingers a sufficient distance, preferably at least a distance of about one inch, from the opening to provide a materially decreased risk of accidentally wounding the fingers with the needle as it is inserted into the body. The device further includes hinge means to hingeably attach a first end of the handle member to the body and provide for hingeable movement of the handle member to a position proximately parallel to the lengthwise central axis of the body, holding means to releasably hold the handle member in a position that the length of the handle is proximately parallel to the lengthwise central axis of the body, and locking means to lock the handle member into a position radial to the lengthwise central axis of the body.

BRIEF DESCRIPTION OF DRAWINGS

FIG. 1 is an elevational view of a safety sheath device of the present invention as fixed on a common disposable syringe.

FIG. 2 is an elevational view illustrating re-applying of the safety sheath device illustrated in FIG. 1 over the needle of the syringe.

FIG. 3 is a perspective view of the safety sheath device illustrated in FIG. 1.

FIG. 4 is a perspective view of a second embodiment of a safety sheath device of the present invention.

FIG. 5 is a perspective view of a third embodiment of a safety sheath device of the present invention.

FIG. 6 is a perspective view of a fourth embodiment of a safety sheath of the present invention with the handle secured in place for use.

FIG. 7 is a perspective view of the safety sheath illustrated in FIG. 6 with the handle folded lengthwise of the sheath for packaging purposes before use.

FIG. 8 is a perspective view of a fifth embodiment of a safety sheath of the present invention.

FIG. 9 is a perspective view of a sixth embodiment of a safety sheath device of the present invention.

DESCRIPTION OF PREFERRED EMBODIMENTS

In FIGS. 1 through 3, safety sheathing device 10 is illustrated and includes hollow body 14 to which is attached integrally molded handle 16 extending outwardly normal from the center lengthwise axis of body 14. Body 14 includes open end 18 to receive insertion of needle 28 to secure the sheath over front needle holding body section 30. Closed end 20 of body sheath 14 is of sufficient length to prevent contact with the encapsulated needle. As shown in FIG. 2, handle 16 of device 10 is held with one hand and opening 22 at end 18 of body 14 is guided toward needle 28 facing the end of needle 28. It is a relatively easy task to guide needle 28 into opening 22 and to force end 18 onto needle holder body 30 to secure device 10 on used syringe 12 which is held in hand 24. As shown in FIG. 3, opening 22 opens to an interior cavity of body 14 which houses and protects the health care worker or persons handling the discarded syringe from accidental contact with needle 28. Surface 32 extends inwardly from the inside surface of body 14 at end 18 to facilitate a force fit and a snap engagement over needle holder body 30. Thus, when device 10 is forced onto and over needle 28 flange 32 snaps over the rearward edge of body 30 to permanently hold device 10 to syringe 12 and allow for safe discard of the used syringe. Handle 16 is a round eighty mil diameter rod about one and one-half inches long, and is part of an integral injection molded part of polyethylene, high density type. The cross-sectional shape of handle 16 is not critical and may be square, hexagonal, rectangular or any other chosen shape. It is important that the combination of cross-section and plastic composition be chosen to provide sufficient strength and rigidity to allow the handle to be held close to the unsupported end and engage the sheath to the syringe.

In FIG. 4, a second embodiment of the invention is illustrated as device 40 which includes hollow body 42 with end opening 44 to receive needle 28 and snap fit over needle holder body 30. In this embodiment, handle 46 extends outwardly from the side of body 42 essentially normal to the lengthwise center axis of body 52 but is constructed in the form of a semi-rigid panel having sufficient thickness and rigidity to allow holding of the end in the fitting and engagement of opening 44 of body 42 over the syringe needle. Handle 46 is a panel about one-quarter inch wide with upper and lower relatively wide surfaces positioned in planes proximately parallel to the lengthwise center axis of body 52. This embodiment allows for a wider area to facilitate holding the device between the fingers of the hand. Handle 56 as shown is about sixty mils thick. The width and thickness may vary considerably with the suitable thickness being thinner as the width is increased. As the width of handle 56 is increased to abut two inches, the approximate length of body 52, the thickness is reduced to a few mils, such as about two to five mils. In this latter embodiment it is possible to roll the handle around body 52 for packaging before use. When opened the elastic memory of the polymeric plastic will cause the handle to spring outwardly allowing the health care worker to grasp the handle well away from opening 54 when re-sheathing the needle. The increased width of handle 56 provides sufficient strength and rigidity to allow re-engagement of the snap detent attachment of device 50.

In FIG. 5, safety sheath 50 includes hollow body 52 which is similar in shape to the bodies described above but has at its open end conical extension 56 opening outwardly and away from open end 54 to provide a wider opening about three-quarters of an one inch in diameter with inclined inside conical surface 58 guiding the point of needle 28 to the center of the opening of body 62 and ultimately allowing snap engagement thereon.

Device 60 illustrated in FIGS. 6 and 7 provides collapsible handle 68 which is folded lengthwise abutting body 62 of the device when it is packaged prior to use. When unpackaged, and before the sheath is removed from the needle of the syringe, handle 68 is pulled outwardly from engagement with formed end 72 in detent holder 74 which holds handle 68 to the body. As handle 68 is pulled outwardly toward a position normal with the lengthwise axis of body 62, it hinges freely on lifetime molded hinge 70 until projection 76 engages into detent lock 78 holding handle 68 permanently and rigidly in position extending outwardly from the body of the device. Device 60 is then removed and when the needle of the syringe is to be re-covered, open end 64 is inserted over the needle while holding handle 68 which when engaged onto the body of the syringe protects the end of the needle by closed end 66 of body 62. In FIG. 8, device 80 illustrates that handle 90 need not be at a ninety degree angle in all planes to the lengthwise axis of body 82. In this embodiment, flat panel 90 is angled away from open end 84 toward end 86 of body 82 by angle A, which is at an angle of about thirty to sixty degrees from the center axis of body 82. In this embodiment, handle 90 still constructed to radiate normally outwardly from the center axis. The planes of panel 90 are still parallel to the center axis. However, it is angled rearwardly to position the hand hold of the person holding the device further away from open end 84 and closer to end 86 which is of sufficient length along the body to prevent contact with the needle of the syringe which cannot reach opening 88 of end 86. In FIG. 9, device 92 illustrates that there can be a plurality of handles, in this case taking the form of four thin handle members 100 radiating outwardly from body 94 at ninety degree angles to each other from the center axis of body 94 which has opening 96 at one end to receive the needle of the syringe and has closed end 98 to protect the user of the device from the end of the needle. Each thin handle member in this embodiment extends about one inch from body 94 closer to the open end and curves backwardly toward the body to terminate proximate closed end 98. In this embodiment, the health care worker can hold any single handle or may hold a plurality of handles without coming close to the needle being inserted in opening 96. Handles 100 in this embodiment are about fifty mils thick which is sufficient to provide rigidity even if only one handle is held. Again, because of the width of handles 100, it being essentially the full length of body 94, the thickness can be substantially reduced, even to two or three mils in which case handles 100 can be all wrapped around body 94 when the device is packaged with the syringe.

All of the safety sheath devices illustrated hereinabove are molded as an integral molding of a thermoplastic polymeric molding composition, such as polyethylene, preferably high density, polypropylene, 6/6 nylon, or like materials. The size and shape of the bodies and the open ends with a detent snap on inside rims are chosen to fit the particular disposable syringe to which the device is to be attached. Typically, the body is about two to three inches long and has an opening of about one-quarter inch in diameter. The handles are chosen to virtually assure that the health care worker can keep his or her fingers well away from the needle and should be about one inch to about three inches in length.

While this invention has been described with reference to the specific embodiments disclosed herein, it is not confined to the details set forth and the patent is intended to include modifications and changes which may come within and extend from the following claims.

I claim:

1. A syringe sheath device to cover and protect the needle of a disposable syringe apparatus having a needle holding housing, the device comprising:
   (a) a hollow body comprising:
      (i) a length, and
      (ii) a first end with an opening to an interior cavity of the body,
   wherein the opening and the interior cavity of the body are of sufficient size and shape to receive insertion of the needle and a portion of the needle holding housing,
   (b) gripping means to grip the needle holding housing and hold the hollow body to the syringe apparatus enclosing the needle,
   (c) a handle member attached to the body,
      (i) extending a direction generally radially to a lengthwise central axis of the body,
      (ii) having sufficient strength and rigidity to allow a person to hold the handle member, insert the needle into the open end of the body, and engage the gripping means to hold the hollow body to the syringe apparatus, and
      (iii) having sufficient length to allow the person to hold the handle member with fingers a sufficient distance from the opening to provide a materially decreased risk of accidentally wounding the fingers with the needle as it is inserted into the body,
   (d) hinge means to hingeably attach a first end of the handle member to the body, to provide for movement of the handle member from a position in juxtaposition with the body proximately parallel to the lengthwise central axis of the body to a position radial to the lengthwise central axis of the body, and
   (e) locking means on the body to lock the handle member into the position radial to the lengthwise central axis of the body.

2. The device of claim 1 wherein the device is a single integral molding of a polymeric plastic.

3. The device of claim 1 wherein the device further comprises holding means to releasably hold the handle member in a position that the length of the handle is proximately parallel to the lengthwise central axis of the body.

4. The device of claim 1 wherein the second end is closed to protect the needle of the syringe inserted therein.

5. The device of claim 1 wherein the rigidity of handle member is sufficient to allow a person gripping the handle to engage the gripping means of the hollow body to hold the needle holding housing of the syringe.

6. A syringe sheath device to cover and protect the needle of a disposable syringe apparatus having a needle holding housing, the device comprising:
   (a) a hollow body comprising:
      (i) a length,
      (ii) a interior cavity of sufficient length to receive the entire length of the needle, and
      (iii) a first end with an opening to the interior cavity of the body,
   wherein the opening and the interior cavity of the body are of sufficient size and shape to receive insertion of the needle and a portion of the needle holding housing,
   (b) gripping means to grip the needle holding housing and hold the hollow body to the syringe enclosing the needle, and
   (c) a handle member attached to the body,
      (i) extending a direction generally radially to a lengthwise central axis of the body,
      (ii) having sufficient strength and rigidity to allow a person to hold the handle member, insert the needle into the open end of the body, and engage the gripping means to hold the hollow body to the syringe apparatus,
      (iii) having sufficient length to allow the person to hold the handle member with fingers a sufficient distance from the opening to provide a materially decreased risk of accidentally wounding the fingers with the needle as it is inserted into the body, (d) hinge means to hingeably attach a first end of the handle member to the body, to provide for movement of the handle member from a position in juxtaposition with the body proximately parallel to the lengthwise central axis of the body to a position radial to the lengthwise central axis of the body, and (e) locking means on the body to lock the handle member into the position radial to the lengthwise central axis of the body.

7. The device of claim 6 wherein the handle member has a length of at least about one inch.

8. The device of claim 6 wherein the device is a single integral molding of a polymeric plastic.

9. The device of claim 6 wherein the device further comprises holding means to releasably hold the handle member in a position that the length of the handle is proximately parallel to the lengthwise central axis of the body.

10. A syringe sheath device to cover and protect the needle of a disposable syringe apparatus having a needle holding housing, the device of a single integral molding of a polymeric plastic comprising:

(a) a hollow body comprising:
  (i) a length,
  (ii) a first end with an opening to an interior cavity of the body, and
  (iii) a second closed end, wherein the opening and the interior cavity of the body are of sufficient size and shape to receive insertion of the needle and a portion of the needle holding housing, (b) gripping means to grip the needle holding housing and hold the hollow body to the syringe apparatus enclosing the needle, and (c) a handle member attached to the body,
  (i) extending a direction generally radially to a lengthwise central axis of the body,
  (ii) having sufficient strength and rigidity to allow a person to hold the handle member, insert the needle into the open end of the body, and engage the gripping means to hold the hollow body to the syringe apparatus, and
  (iii) having sufficient length to allow the person to hold the handle member with fingers at least a distance of about one inch from the opening to provide a materially decreased risk of accidentally wounding the fingers with the needle as it is inserted into the body (d) hinge means to hingeably attach a first end of the handle member to the body and provide for hingeable movement of the handle member from a position in juxtaposition with the body proximately parallel to the lengthwise central axis of the body to a position radial to the lengthwise central axis of the body, (e) holding means to releasably hold the handle member in a position that the length of the handle is proximately parallel to the lengthwise central axis of the body, and (f) locking means on the body to lock the handle member into the position radial to the lengthwise central axis of the body.

11. The device of claim 10 wherein the handle member has a length of at least about one inch.

12. The device of claim 10 wherein the device is a single integral molding of a polymeric plastic.

* * * * *